US011793492B2

(12) United States Patent
Zhang et al.

(10) Patent No.: US 11,793,492 B2
(45) Date of Patent: Oct. 24, 2023

(54) METHODS AND SYSTEMS FOR PERFORMING COLOR DOPPLER ULTRASOUND IMAGING

(71) Applicant: KONINKLIJKE PHILIPS N.V., Eindhoven (NL)

(72) Inventors: Bo Zhang, Paris (FR); Odile Bonnefous, Rueil-Malmaison (FR)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 479 days.

(21) Appl. No.: 17/256,384

(22) PCT Filed: Jun. 24, 2019

(86) PCT No.: PCT/EP2019/066567
§ 371 (c)(1),
(2) Date: Dec. 28, 2020

(87) PCT Pub. No.: WO2020/002171
PCT Pub. Date: Jan. 2, 2020

(65) Prior Publication Data
US 2021/0369245 A1 Dec. 2, 2021

(30) Foreign Application Priority Data
Jun. 28, 2018 (EP) .................................. 18290072

(51) Int. Cl.
*A61B 8/06* (2006.01)
*A61B 8/08* (2006.01)

(52) U.S. Cl.
CPC .............. *A61B 8/5253* (2013.01); *A61B 8/06* (2013.01); *A61B 8/483* (2013.01); *A61B 8/488* (2013.01)

(58) Field of Classification Search
CPC ......... A61B 8/5253; A61B 8/06; A61B 8/483; A61B 8/488; A61B 8/0883; A61B 8/0891; A61B 8/14
See application file for complete search history.

(56) References Cited

U.S. PATENT DOCUMENTS

| 9,414,805 B2 * | 8/2016 | Ustuner .............. G01S 7/52066 |
| 2004/0059220 A1 * | 3/2004 | Mourad ................. A61B 8/485 600/442 |

(Continued)

FOREIGN PATENT DOCUMENTS

| EP | 3111850 A1 | 1/2017 |
| JP | 2006000421 A | 1/2006 |

OTHER PUBLICATIONS

Gomez, et al., "4D Blood Flow Reconstruction Over the Entire Ventricle From Wall Motion and Blood Velocity Derived From Ultrasound Data", IEEE Transactions on Medical Imaging, vol. 34, No. 11, Nov. 2015, pp. 2298-2308.

Gomez, et al., "3D Intraventricular Flow Mapping from Colour Doppler Images and Wall Motion", Research Gate, Conference Paper, Sep. 2013, pp. 1-8.

(Continued)

*Primary Examiner* — Bo Joseph Peng

(57) ABSTRACT

The invention provides a color Doppler ultrasound imaging method. The method includes acquiring a plurality of sparse color Doppler ultrasound image frames and B-mode ultrasound image frames. The color Doppler and B-mode image frames are then pre-processed before estimating a vector flow based on said frames by means of solving a flow vector field in a whole field of view of the image frames through an optimization framework, in which a mask is adapted to define a sparse area of observed color Doppler measurements within the sparse color Doppler image frames. A new color Doppler image frame is generated based on this estimate and included in the output image.

16 Claims, 3 Drawing Sheets

3. Vector Flow from Div(V)=0

300

(56) References Cited

U.S. PATENT DOCUMENTS

| | | | |
|---|---|---|---|
| 2005/0015009 A1* | 1/2005 | Mourad | A61B 5/0051 600/453 |
| 2008/0269611 A1* | 10/2008 | Pedrizzetti | G01S 7/52071 382/128 |
| 2011/0218435 A1 | 9/2011 | Srinivasan et al. | |
| 2012/0014588 A1* | 1/2012 | Chono | A61B 8/00 382/133 |
| 2012/0215110 A1* | 8/2012 | Wilkening | G01S 7/52095 600/453 |
| 2014/0018683 A1 | 1/2014 | Park et al. | |
| 2015/0141832 A1 | 5/2015 | Yu et al. | |
| 2016/0310110 A1* | 10/2016 | Dodd | A61B 8/54 |
| 2018/0088220 A1* | 3/2018 | Flynn | G01S 15/8979 |
| 2018/0146952 A1 | 5/2018 | Du et al. | |
| 2019/0365355 A1* | 12/2019 | Eldar | A61B 8/488 |
| 2019/0380684 A1* | 12/2019 | Insana | G01S 15/8981 |
| 2021/0353251 A1* | 11/2021 | Hope Simpson | A61B 8/14 |
| 2021/0369236 A1* | 12/2021 | Bonnefous | A61B 8/0883 |

OTHER PUBLICATIONS

Assi, et al., "Intraventricular vector low mapping—a Doppler-based regularized problem with automatic model selection", Institute of Physics and Engineering in Medicine, Physics in Medicine and Biology, 62 (2017), pp. 7131-7147.

Itatani, et al., "Intraventicular Flow Velocity Vector Visualization Based on the Continuity Equation and Measurements of Vorticity and Wall Shear Stress", Japanese Journal of Applied Physics 52, 2013, pp. 07HF16-1 to 07HF16-6.

International Search Report and Written Opinion for International Application No. PCT/EP2019/066567, filed Jun. 24, 2019, 13 pages.

D. Garcia et al., "Two-dimensional intraventricular flow mapping by digital processing conventional color—Doppler echocardiography images," IEEE Trans. Med. Imag., vol. 29, No. 10, pp. 1701-1713, Oct. 2010.

Osmanski, et al., "Ultrafast imaging of blood flow dynamics in the myocardium," IEEE Transactions on Medical Imaging 31, No. 8 (2012): 1661-1668. (Abstract).

Itoh, "Analysis of the phase unwrapping problem," Applied Optics, vol. 21, No. 14, p. 2470, Jul. 15, 1982. (Abstract).

Jensen, J., "Spectral velocity estimation in ultrasound using sparse data sets", J. Acoustical Society of America, vol. 120, No. 1, pp. 211-220.

* cited by examiner 1. 2D Color Doppler                                    Volume nb:1
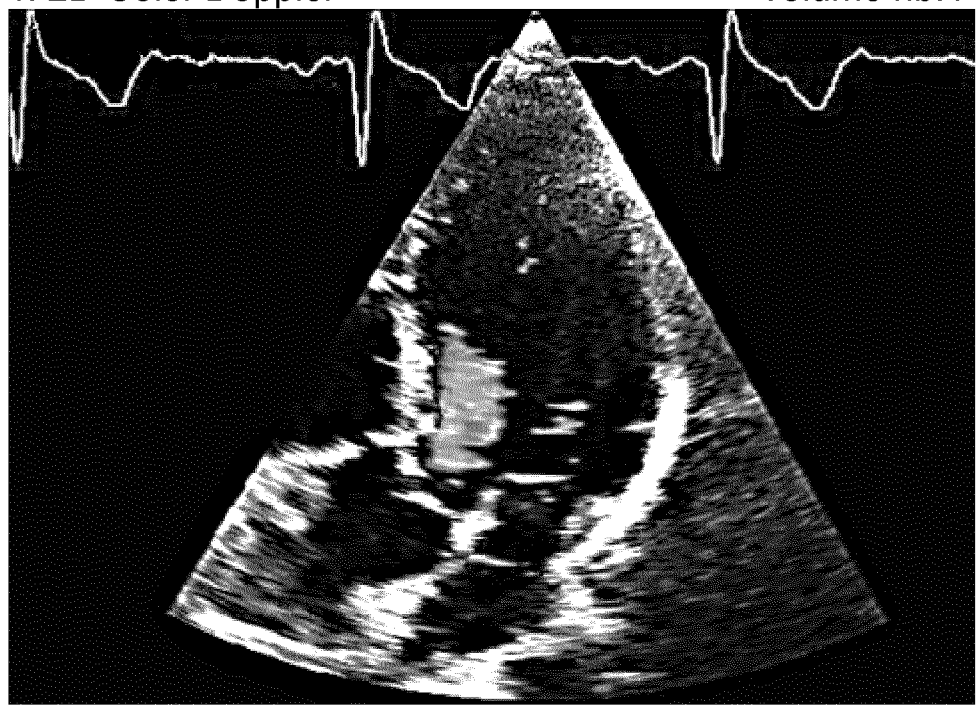
FIG. 3a  ← 300
3. Vector Flow from Div(V)=0
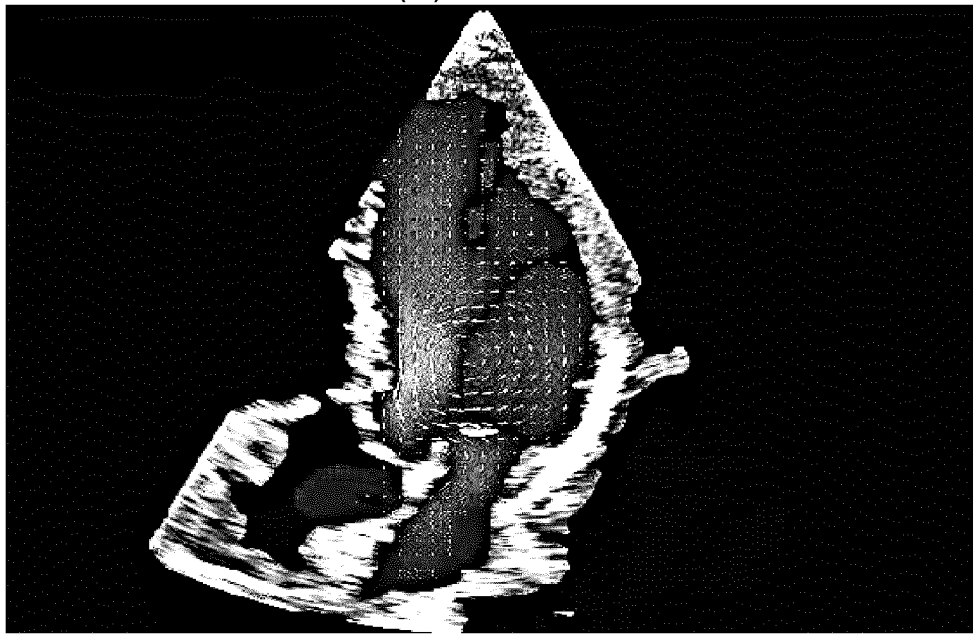
FIG. 3b  ← 300

METHODS AND SYSTEMS FOR PERFORMING COLOR DOPPLER ULTRASOUND IMAGING

RELATED APPLICATIONS

This application is the U.S. National Phase application under 35 U.S.C. § 371 of International Application No. PCT/EP2019/066567, filed on Jun. 24, 2019, which claims priority to and the benefit of European Application No. 18290072.0, filed Jun. 28, 2018, which are incorporated by reference in their entireties.

FIELD OF THE INVENTION

This invention relates to the field of ultrasound imaging, and in particular to the field of color Doppler ultrasound imaging.

BACKGROUND OF THE INVENTION

Color Doppler ultrasound imaging allows the user to visualize the flow information along the ultrasound beam. This functionality has become widely deployed in today's echography systems.

When one desires to visualize color Doppler ultrasound information in a large field of view, the frame rate typically drops, as measures need to be taken at an increasing number of spatial points.

In order to decrease the framerate penalization, it has been previously proposed to resort to an ultrafast scanning scheme, based on plane or divergent waves. However, this requires a redesign of the ultrafast acquisition sequence and adaptation of the front end of the ultrasound imaging system for ultrafast use. Therefore, this proposal may not be readily usable on an existing system that does not possess ultrafast scanning capability.

There is therefore a need to provide a color Doppler ultrasound imaging method capable of imaging a large field of view without requiring significant additional hardware.

EP 3 111 850 A1 discloses an ultrasound diagnostic apparatus that utilizes blood-flow velocity information obtained by the color Doppler method and estimates a three-dimensional effect of the blood flow, so as to present diagnostic information into which the estimated three-dimensional effect is reflected.

SUMMARY OF THE INVENTION

The invention is defined by the claims.

According to examples in accordance with an aspect of the invention, there is provided a color Doppler ultrasound imaging method, the method comprising:

acquiring a plurality of sparse color Doppler ultrasound image frames and B-mode ultrasound image frames;

pre-processing a current sparse color Doppler ultrasound image frame and a B-mode ultrasound image frame of the plurality of sparse color Doppler and B-mode ultrasound image frames;

estimating a vector flow based on the pre-processed current sparse color Doppler and B-mode ultrasound image frames;

generating a new color Doppler image frame based on the estimated vector flow; and generating an output image including the new color Doppler image frame.

In accordance with this aspect of the invention, the estimating of a vector flow comprises solving a flow vector field in a whole field of view of the image frames by applying an optimization framework to the current sparse color Doppler image frame. Moreover, the optimization framework comprises a mask adapted to define a sparse area of observed color Doppler measurements within the current sparse color Doppler image frame, such that the solved flow vector field is compatible with the observed color Doppler measurements within the mask.

This method provides for an increased frame rate when performing color Doppler ultrasound imaging of a large field of view.

Typically, color Doppler images are incomplete, or sparse, due to loss of information during the imaging process, for example due to a wall filter intended to separate blood flow from tissue movement. That is, the sparse color Doppler images are typically incomplete because they do not contain color Doppler measurements for the whole field of view of the image frames, but only for a reduced and sparse area within said field of view.

By performing an estimation of the vector flow, it is possible to use post-processing to acquire complete color Doppler ultrasound images with a large field of view without requiring the use of ultrafast scanning techniques, which often requires significant amounts of additional front-end hardware.

By applying a mask to the areas of sparse measurement, the estimation of the vector flow is constrained to areas where color Doppler image data exists and is not extended to areas of the B-mode image where said data may be entirely absent. In this way, the accuracy of the final color Doppler image is increased as no estimations are performed in the total absence of data. In other words, the estimated vector flow remains compatible with the observed color Doppler ultrasound image frames. The mask is defined to be the area of the color Doppler image frame where the measured Doppler signal is nonzero.

In an embodiment, the generating of an output image comprises overlaying the new color Doppler image frame on the current B-mode ultrasound image frame.

In this way, the new color Doppler image frame is given structural context by the B-mode ultrasound image frame, thereby making the output image easier for the user to interpret.

In an embodiment, the generating of a new color Doppler image frame comprises re-projecting the flow vector field solved in the whole field of view of the image frames on the ultrasound beam orientation along which the observed color Doppler measurements have been acquired.

In this way, the new color Doppler image frame is filled with the color information that was previously missing in the current sparse color Doppler ultrasound image frame.

In an arrangement, the pre-processing comprises performing phase unwrapping on the current sparse color Doppler ultrasound image frame.

In this way, the relative phases of all of the received signals may be assessed without the restrictions imposed by a wrapped phase signal (which are typically constrained to a range of 2 pi).

In an embodiment, the pre-processing comprises performing flow boundary segmentation on the current B-mode ultrasound image frame.

In a further embodiment, the pre-processing comprises deriving a motion of a boundary between a previous B-mode image frame and the current B-mode frame based on the flow boundary segmentation.

In this way, the motion of the structures in the field of view, for example the walls of a heart, may be monitored in order to determine a boundary motion, which will in turn affect the vector flow. By taking this into account, the accuracy of the final image is increased.

In an arrangement, the derivation of the motion of the boundary is based on speckle tracking.

In a further embodiment, the optimization framework comprises a smoothing term.

The smoothing term may increase the accuracy of the B-mode image frame by reducing or removing any imaging artefacts present in the frame. The smoothing term increases the stability of the optimization framework when generating a numerical solution, thereby increasing the robustness of the optimization framework against measurement inaccuracies.

In a further embodiment, the optimization framework comprises a zero divergence restraint.

The zero divergence restraint prevents additional fluid (blood) from being erroneously added to the system. In other words, the mass of the fluid is conserved.

In a further, or other, embodiment the optimization framework comprises an estimated boundary velocity.

In this way, the estimated vector flow takes account of boundary velocity (which is particularly relevant in a beating heart), thereby increasing the accuracy of the final image. The estimated vector flow may be constrained to match the boundary velocity in the vicinity of the boundary.

In a further embodiment, the mask is a pixel-wise weighting mask having a value of zero for each of those pixels in the current sparse color Doppler image frame for which no observed color Doppler measurement exist.

In such an embodiment, the weighting mask may preferably have a value ranging between zero and one for each of those pixels in the current sparse color Doppler image frame for which observed color Doppler measurement exist, said value reflecting a confidence level on the observed color Doppler measurement at each respective pixel. In some examples, the value of the weighting mask for any pixel for which observed color Doppler measurement exist may be strictly larger than zero and strictly smaller than one, while in some other embodiments said value may range from being equal to zero to being equal to one.

In particular, the confidence level may be a function of the noise level at each respective pixel.

In this way, the contribution of pixels for which the confidence level on the observed color Doppler measurement is low (e.g. due to noise) to the optimization framework to solve the flow vector field can be reduced or even suppressed (e.g., by making the value of the weighting mask equal to zero), while the contribution of pixels having high confidence level can be enhanced (e.g., by making the value of the weighting mask close to or even equal to one).

In an arrangement, the plurality of sparse color Doppler ultrasound image frames comprises 3D color Doppler ultrasound image volumes.

In a further arrangement, the 3D color Doppler ultrasound image volumes are generated by:
acquiring a set of sparse color Doppler ultrasound image frames at a plurality of spatial locations;
interpolating image data between the acquired frames of the sets of sparse color Doppler ultrasound image frames; and
generating 3D color Doppler image volumes based on the acquired image frames and the interpolated image data.

In this way, the processing power required to perform 3D color Doppler imaging is reduced, thereby maintaining the frame rate improvement offered by the method described above.

According to examples in accordance with an aspect of the invention, there is provided a computer program comprising computer program code means which is adapted, when said computer program is run on a computer, to implement the method described above.

According to examples in accordance with an aspect of the invention, there is provided an ultrasound system adapted to perform color Doppler ultrasound imaging, the system comprising:
an ultrasound probe adapted to acquire ultrasound image data;
a processor adapted to:
acquire a plurality of sparse color Doppler ultrasound image frames and B-mode ultrasound image frames;
pre-process a current sparse color Doppler ultrasound image frame and a B-mode ultrasound image frame of the plurality of sparse color Doppler and B-mode ultrasound image frames;
estimate a vector flow based on the pre-processed current sparse color Doppler and B-mode ultrasound image frames;
generate a new color Doppler image frame based on the estimated vector flow; and
generate an output image including the new color Doppler image frame.

In accordance with this aspect of the invention, estimating a vector flow comprises solving a flow vector field in a whole field of view of the image frames by applying an optimization framework to the current sparse color Doppler image frame. Moreover, the optimization framework comprises a mask adapted to define a sparse area of observed color Doppler measurements within the current sparse color Doppler image frame, such that the solved flow vector field is compatible with the observed color Doppler measurements within the mask.

These and other aspects of the invention will be apparent from and elucidated with reference to the embodiment(s) described hereinafter.

BRIEF DESCRIPTION OF THE DRAWINGS

Examples of the invention will now be described in detail with reference to the accompanying drawings, in which:

FIGS. 3a and 3b show a comparison between a sparse color Doppler image frame and the corresponding new color Doppler image frame overlain on the associated B-mode image.

DETAILED DESCRIPTION OF THE EMBODIMENTS

Figure 1:
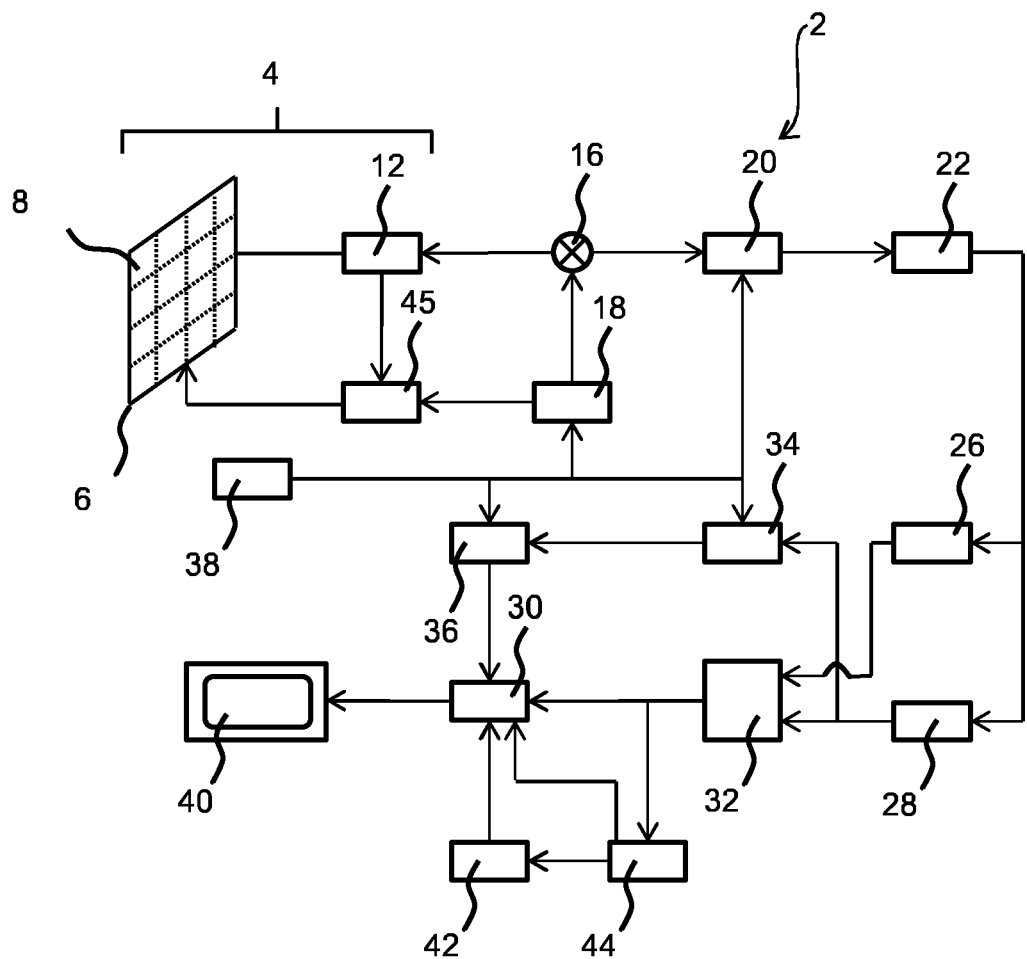
FIG. 1 shows an ultrasound diagnostic imaging system to explain the general operation.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides a color Doppler ultrasound imaging method. The method includes acquiring a plurality of sparse color Doppler ultrasound image frames and B-mode ultrasound image frames. The color Doppler and B-mode image frames are then pre-processed before estimating a vector flow based on said frames. A new color Doppler image frame is generated based on this estimate and included in the output image.

The general operation of an exemplary ultrasound system will first be described, with reference to FIG. 1, and with emphasis on the signal processing function of the system since this invention relates to the processing of the signals measured by the transducer array.

The system comprises an array transducer probe 4 which has a transducer array 6 for transmitting ultrasound waves and receiving echo information. The transducer array 6 may comprise CMUT transducers; piezoelectric transducers, formed of materials such as PZT or PVDF; or any other suitable transducer technology. In this example, the transducer array 6 is a two-dimensional array of transducers 8 capable of scanning either a 2D plane or a three dimensional volume of a region of interest. In another example, the transducer array may be a 1D array.

The transducer array 6 is coupled to a microbeamformer 12 which controls reception of signals by the transducer elements. Microbeamformers are capable of at least partial beamforming of the signals received by sub-arrays, generally referred to as "groups" or "patches", of transducers as described in U.S. Pat. No. 5,997,479 (Savord et al.), U.S. Pat. No. 6,013,032 (Savord), and U.S. Pat. No. 6,623,432 (Powers et al.).

It should be noted that the microbeamformer is entirely optional. Further, the system includes a transmit/receive (T/R) switch 16, which the microbeamformer 12 can be coupled to and which switches the array between transmission and reception modes, and protects the main beamformer 20 from high energy transmit signals in the case where a microbeamformer is not used and the transducer array is operated directly by the main system beamformer. The transmission of ultrasound beams from the transducer array 6 is directed by a transducer controller 18 coupled to the microbeamformer by the T/R switch 16 and a main transmission beamformer (not shown), which can receive input from the user's operation of the user interface or control panel 38. The controller 18 can include transmission circuitry arranged to drive the transducer elements of the array 6 (either directly or via a microbeamformer) during the transmission mode.

In a typical line-by-line imaging sequence, the beamforming system within the probe may operate as follows. During transmission, the beamformer (which may be the microbeamformer or the main system beamformer depending upon the implementation) activates the transducer array, or a sub-aperture of the transducer array. The sub-aperture may be a one dimensional line of transducers or a two dimensional patch of transducers within the larger array. In transmit mode, the focusing and steering of the ultrasound beam generated by the array, or a sub-aperture of the array, are controlled as described below.

Upon receiving the backscattered echo signals from the subject, the received signals undergo receive beamforming (as described below), in order to align the received signals, and, in the case where a sub-aperture is being used, the sub-aperture is then shifted, for example by one transducer element. The shifted sub-aperture is then activated and the process repeated until all of the transducer elements of the transducer array have been activated.

For each line (or sub-aperture), the total received signal, used to form an associated line of the final ultrasound image, will be a sum of the voltage signals measured by the transducer elements of the given sub-aperture during the receive period. The resulting line signals, following the beamforming process below, are typically referred to as radio frequency (RF) data. Each line signal (RF data set) generated by the various sub-apertures then undergoes additional processing to generate the lines of the final ultrasound image. The change in amplitude of the line signal with time will contribute to the change in brightness of the ultrasound image with depth, wherein a high amplitude peak will correspond to a bright pixel (or collection of pixels) in the final image. A peak appearing near the beginning of the line signal will represent an echo from a shallow structure, whereas peaks appearing progressively later in the line signal will represent echoes from structures at increasing depths within the subject.

One of the functions controlled by the transducer controller 18 is the direction in which beams are steered and focused. Beams may be steered straight ahead from (orthogonal to) the transducer array, or at different angles for a wider field of view. The steering and focusing of the transmit beam may be controlled as a function of transducer element actuation time.

Two methods can be distinguished in general ultrasound data acquisition: plane wave imaging and "beam steered" imaging. The two methods are distinguished by a presence of the beamforming in the transmission ("beam steered" imaging) and/or reception modes (plane wave imaging and "beam steered" imaging).

Looking first to the focusing function, by activating all of the transducer elements at the same time, the transducer array generates a plane wave that diverges as it travels through the subject. In this case, the beam of ultrasonic waves remains unfocused. By introducing a position dependent time delay to the activation of the transducers, it is possible to cause the wave front of the beam to converge at a desired point, referred to as the focal zone. The focal zone is defined as the point at which the lateral beam width is less than half the transmit beam width. In this way, the lateral resolution of the final ultrasound image is improved.

For example, if the time delay causes the transducer elements to activate in a series, beginning with the outermost elements and finishing at the central element(s) of the transducer array, a focal zone would be formed at a given distance away from the probe, in line with the central element(s). The distance of the focal zone from the probe will vary depending on the time delay between each subsequent round of transducer element activations. After the beam passes the focal zone, it will begin to diverge, forming the far field imaging region. It should be noted that for focal zones located close to the transducer array, the ultrasound beam will diverge quickly in the far field leading to beam width artifacts in the final image. Typically, the near field, located between the transducer array and the focal zone, shows little detail due to the large overlap in ultrasound beams. Thus, varying the location of the focal zone can lead to significant changes in the quality of the final image.

It should be noted that, in transmit mode, only one focus may be defined unless the ultrasound image is divided into multiple focal zones (each of which may have a different transmit focus).

In addition, upon receiving the echo signals from within the subject, it is possible to perform the inverse of the above described process in order to perform receive focusing. In other words, the incoming signals may be received by the transducer elements and subject to an electronic time delay before being passed into the system for signal processing. The simplest example of this is referred to as delay-and-sum beamforming. It is possible to dynamically adjust the receive focusing of the transducer array as a function of time.

Looking now to the function of beam steering, through the correct application of time delays to the transducer elements it is possible to impart a desired angle on the ultrasound beam as it leaves the transducer array. For example, by activating a transducer on a first side of the transducer array followed by the remaining transducers in a sequence ending at the opposite side of the array, the wave front of the beam will be angled toward the second side. The size of the steering angle relative to the normal of the transducer array is dependent on the size of the time delay between subsequent transducer element activations.

Further, it is possible to focus a steered beam, wherein the total time delay applied to each transducer element is a sum of both the focusing and steering time delays. In this case, the transducer array is referred to as a phased array.

In case of the CMUT transducers, which require a DC bias voltage for their activation, the transducer controller 18 can be coupled to control a DC bias control 45 for the transducer array. The DC bias control 45 sets DC bias voltage(s) that are applied to the CMUT transducer elements.

For each transducer element of the transducer array, analog ultrasound signals, typically referred to as channel data, enter the system by way of the reception channel. In the reception channel, partially beamformed signals are produced from the channel data by the microbeamformer 12 and are then passed to a main receive beamformer 20 where the partially beamformed signals from individual patches of transducers are combined into a fully beamformed signal, referred to as radio frequency (RF) data. The beamforming performed at each stage may be carried out as described above, or may include additional functions. For example, the main beamformer 20 may have 128 channels, each of which receives a partially beamformed signal from a patch of dozens or hundreds of transducer elements. In this way, the signals received by thousands of transducers of a transducer array can contribute efficiently to a single beamformed signal.

The beamformed reception signals are coupled to a signal processor 22. The signal processor 22 can process the received echo signals in various ways, such as: band-pass filtering; decimation; I and Q component separation; and harmonic signal separation, which acts to separate linear and nonlinear signals so as to enable the identification of nonlinear (higher harmonics of the fundamental frequency) echo signals returned from tissue and micro-bubbles. The signal processor may also perform additional signal enhancement such as speckle reduction, signal compounding, and noise elimination. The band-pass filter in the signal processor can be a tracking filter, with its pass band sliding from a higher frequency band to a lower frequency band as echo signals are received from increasing depths, thereby rejecting noise at higher frequencies from greater depths that is typically devoid of anatomical information.

The beamformers for transmission and for reception are implemented in different hardware and can have different functions. Of course, the receiver beamformer is designed to take into account the characteristics of the transmission beamformer. In FIG. 1 only the receiver beamformers 12, 20 are shown, for simplicity. In the complete system, there will also be a transmission chain with a transmission micro beamformer, and a main transmission beamformer.

The function of the micro beamformer 12 is to provide an initial combination of signals in order to decrease the number of analog signal paths. This is typically performed in the analog domain.

The final beamforming is done in the main beamformer 20 and is typically after digitization.

The transmission and reception channels use the same transducer array 6 which has a fixed frequency band. However, the bandwidth that the transmission pulses occupy can vary depending on the transmission beamforming used. The reception channel can capture the whole transducer bandwidth (which is the classic approach) or, by using bandpass processing, it can extract only the bandwidth that contains the desired information (e.g. the harmonics of the main harmonic).

The RF signals may then be coupled to a B mode (i.e. brightness mode, or 2D imaging mode) processor 26 and a Doppler processor 28. The B mode processor 26 performs amplitude detection on the received ultrasound signal for the imaging of structures in the body, such as organ tissue and blood vessels. In the case of line-by-line imaging, each line (beam) is represented by an associated RF signal, the amplitude of which is used to generate a brightness value to be assigned to a pixel in the B mode image. The exact location of the pixel within the image is determined by the location of the associated amplitude measurement along the RF signal and the line (beam) number of the RF signal. B mode images of such structures may be formed in the harmonic or fundamental image mode, or a combination of both as described in U.S. Pat. No. 6,283,919 (Roundhill et al.) and U.S. Pat. No. 6,458,083 (Jago et al.) The Doppler processor 28 processes temporally distinct signals arising from tissue movement and blood flow for the detection of moving substances, such as the flow of blood cells in the image field. The Doppler processor 28 typically includes a wall filter with parameters set to pass or reject echoes returned from selected types of materials in the body.

The structural and motion signals produced by the B mode and Doppler processors are coupled to a scan converter 32 and a multi-planar reformatter 44. The scan converter 32 arranges the echo signals in the spatial relationship from which they were received in a desired image format. In other words, the scan converter acts to convert the RF data from a cylindrical coordinate system to a Cartesian coordinate system appropriate for displaying an ultrasound image on an image display 40. In the case of B mode imaging, the brightness of pixel at a given coordinate is proportional to the amplitude of the RF signal received from that location. For instance, the scan converter may arrange the echo signal into a two dimensional (2D) sector-shaped format, or a pyramidal three dimensional (3D) image. The scan converter can overlay a B mode structural image with colors corresponding to motion at points in the image field, where the Doppler-estimated velocities to produce a given color. The combined B mode structural image and color Doppler image depicts the motion of tissue and blood flow within the structural image field. The multi-planar reformatter will convert echoes that are received from points in a common plane in a volumetric region of the body into an ultrasound image of that plane, as described in U.S. Pat. No. 6,443,896 (Detmer). A volume renderer 42 converts the echo signals of a 3D data set into a projected 3D image as viewed from a given reference point as described in U.S. Pat. No. 6,530,885 (Entrekin et al.).

The 2D or 3D images are coupled from the scan converter 32, multi-planar reformatter 44, and volume renderer 42 to an image processor 30 for further enhancement, buffering and temporary storage for display on an image display 40. The imaging processor may be adapted to remove certain imaging artifacts from the final ultrasound image, such as: acoustic shadowing, for example caused by a strong attenuator or refraction; posterior enhancement, for example caused by a weak attenuator; reverberation artifacts, for example where highly reflective tissue interfaces are located in close proximity; and so on. In addition, the image processor may be adapted to handle certain speckle reduction functions, in order to improve the contrast of the final ultrasound image.

In addition to being used for imaging, the blood flow values produced by the Doppler processor 28 and tissue structure information produced by the B mode processor 26 are coupled to a quantification processor 34. The quantification processor produces measures of different flow conditions such as the volume rate of blood flow in addition to structural measurements such as the sizes of organs and gestational age. The quantification processor may receive input from the user control panel 38, such as the point in the anatomy of an image where a measurement is to be made.

Output data from the quantification processor is coupled to a graphics processor 36 for the reproduction of measurement graphics and values with the image on the display 40, and for audio output from the display device 40. The graphics processor 36 can also generate graphic overlays for display with the ultrasound images. These graphic overlays can contain standard identifying information such as patient name, date and time of the image, imaging parameters, and the like. For these purposes the graphics processor receives input from the user interface 38, such as patient name. The user interface is also coupled to the transmit controller 18 to control the generation of ultrasound signals from the transducer array 6 and hence the images produced by the transducer array and the ultrasound system. The transmit control function of the controller 18 is only one of the functions performed. The controller 18 also takes account of the mode of operation (given by the user) and the corresponding required transmitter configuration and band-pass configuration in the receiver analog to digital converter. The controller 18 can be a state machine with fixed states.

The user interface is also coupled to the multi-planar reformatter 44 for selection and control of the planes of multiple multi-planar reformatted (MPR) images which may be used to perform quantified measures in the image field of the MPR images.

Figure 2:
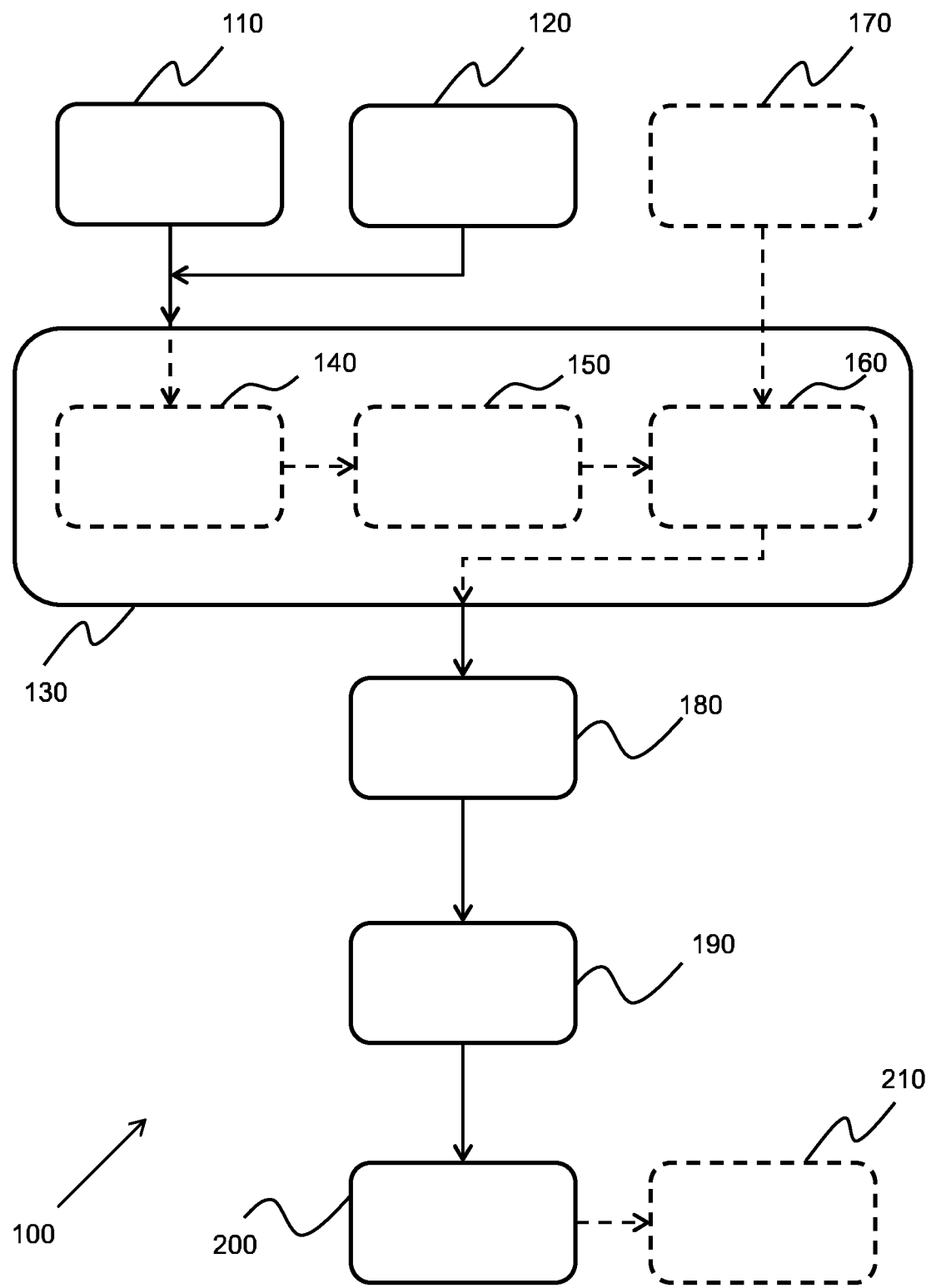
FIG. 2 shows a method of the invention.

FIG. 2 shows a method 100 of this invention.

In steps 110 and 120, a plurality of sparse color Doppler ultrasound image frames and B-mode ultrasound image frames are acquired, respectively. The image frames may be acquired as described above with reference to FIG. 1.

Typically, the color Doppler image frames will be incomplete, or sparse, due to loss of information during the imaging process, for example due to a wall filter intended to separate blood flow from tissue movement.

Of the plurality of acquired color Doppler and B-mode image frames, one image frame of each type (for example the most recently acquired image frames) undergo a pre-processing step 130.

The current sparse color Doppler frame may be denoted as m, and is overlaid on the corresponding B-mode frame, which is denoted as v. The overlaying of the color Doppler frame on the B-mode frame allows the structural information contained within the B-mode image to be used in conjunction with the flow information contained in the color Doppler frame.

In step 140, phase unwrapping is performed on the Doppler frame m.

Typically, the signal phase of time-varying functions is represented in an interval of $(-\pi, \pi)$ or $(0, 2\pi)$, wherein signals with phases outside of this interval are cut-off at one boundary and begin again at the other. This can result in discontinuities in the form of Dirac delta impulses in the signal, which may result in artifacts in the final image. By performing phase unwrapping, the restraints are removed from the signal and these discontinuities are avoided. The phase unwrapping may be performed as described in K. Itoh, "Analysis of the phase unwrapping problem," Applied Optics, Vol. 21, No. 14, p. 2470, Jul. 15, 1982.

In step 150, flow boundary segmentation is performed on the B-mode image frame.

The segmentation identifies the boundaries within the image that control the flow shown in the color Doppler image frame. By identifying these boundaries, it is possible to confine the future vector flow estimation to only the areas where a fluid flow is possible, thereby increasing the efficiency of the method. The segmentation may be performed based on signal intensity threshold or through any other suitable method.

In step 160, the motion of the segmented flow boundaries may be derived based on the current B-mode image frame and a previous B-mode image frame 170, such as the B-mode frame acquired immediately previous to the current B-mode image frame.

The motion of the flow boundaries, which is denoted as $v_0$, play an important part in the full vector flow of a regions, particularly when the imaging is being performed on a heart. The motion of the flow boundaries may be tracked from frame to frame based on speckle tracking.

In step 180, a vector flow rate is estimated based on the pre-processed color Doppler and B-mode image frames, m and v.

The vector flow estimation is solved through an optimization framework. To solve the flow vector field u, the following framework is minimized:

$$\underset{\nabla \cdot u = 0, u(B) = v_0}{\mathrm{argmin}} \quad J(u) = \|M[\langle s, u \rangle - m]\|^2 + \lambda_S \|\nabla u\|^2$$

where: s is the ultrasonic beam orientation along which the color Doppler image frame measurements m are acquired; M denotes a mask, also referred to as a confidence mask, which defines the sparse area of observed measurement within the color Doppler image frame; B is the flow boundary (tissue) given by the segmentation, on which the boundary velocity v is estimated; and $\lambda_S$ represents the weight of the smoothing term $\|\nabla\|u^2$.

The term $\|M[\langle s, u \rangle - m]\|^2$ restricts the flow solution of the vector field u to be compatible with the Doppler measurements, m. For any pixel, x, on the color Doppler image frame, u(x) is the flow vector at said pixel to be solved. The projection of the flow vector u(x) on the Doppler beam orientation vector s(x) at the same pixel is described by their inner product $\langle s(x), u(x) \rangle$. This product is calculated to be as close as possible to the true Doppler measurement at a given pixel. The term $\langle s, u \rangle - m$ is referred to as a difference image and represents the difference between the Doppler measurements, m, and the inner product of the flow vector u(x) and the Doppler beam orientation vector s(x).

M is a pixel-wise weighting mask that describes the confidence of each Doppler measurement at each location on the color Doppler image frame. It is applied on the difference image, ⟨s, u⟩−m. In the simplest case, at pixel x, M(x) is either 0 or 1. As not all pixels have Doppler velocity measurements, only pixels with available measurements will have M(x)=1. The others will have a value of 0 (as no measurement exists). More generally, M(x) ranges between 0 and 1, to reflect prior confidence levels on the Doppler measure at pixel x (for example, as a function of the noise level). For this reason, this first term, $\|M[\langle s, u\rangle-m]\|^2$, should be minimized.

The term $\|\nabla u\|^2$ is for regularization, or smoothing, such that the numerical solution of the equation may be more stable. $\lambda_S$ is a scalar that adjusts the trade-off between the compatibility term (described below) and the smoothing term.

Constraint $u(B)=v_0$, also referred to as the compatibility term, requires the flow solution to be compatible with the boundary condition. The boundary pixel set is specified by B. $v_0$ is the boundary velocity that may be derived as described above, for example using speckle-tracking.

Constraint $\nabla \cdot u=0$ reflects the restriction that the flow solution should be divergence free due to mass conservation.

The equation is solved using an Augmented Lagrangian method; however, other standard numerical methods for convex minimization, such as projected gradient descent, may also be applied.

In other words, the vector flow is solved in the whole field of view such that: the vector flow is compatible with the observed color Doppler measurements within the confidence mask M; the mass preservation of the fluid within the field of view is respected through a zero divergence constraint ($\nabla \cdot u=0$); and the solution is compatible with the estimated the boundary velocity ($u(B)=v_0$).

In step 190, a new color Doppler image frame is generated based on the estimated vector flow.

Once the vector field u is estimated in the whole field of view, the flow vector may be re-projected on the beam orientation s to form a new color Doppler image frame, where the previously missing color information is filled. This may then be used to form an output image in step 200.

In step 210, the new color Doppler image frame may be overlain on the current B-mode image frame in order to provide the user with complete color Doppler information in addition to the structural context of the imaging area.

As described in the method so far, the image frames have been assumed to be 2D; however, this method may be extended to 3D color acquisition where the frame rate impact is even more significant due to the significantly larger number of measurements required.

In this case, the plurality of color Doppler image frames comprises 3D color Doppler image volumes.

In order to accelerate the acquisition of the 3D color Doppler, a set of sparse color Doppler ultrasound image frames are acquired at a plurality of spatial locations.

The sparse color Doppler color data is then interpolated in space and time, for example by way of the Navier Stokes equation, and used in combination with the acquired frames to form the 3D color Doppler image volumes. This reduces the number of measurements required to acquire the 3D image volumes necessary to perform 3D color Doppler imaging, which results in a higher frame rate. The 3D color Doppler image volumes may then be combined with 3D B-mode ultrasound volumes, acquired in a conventional 3D imaging mode.

FIG. 3*a* shows an example of a sparse color Doppler image frame 300 where color information is measured only partially within the heart cavity. FIG. 3*b* shows the vector flow estimate, in the form of vector arrows, and the refilled color of the new color Doppler image frame. It can be seen that the whole ventricle area is now filled with color information, which is visually consistent with the sparse measurements shown in FIG. 3*a*. In this example, the observed sparse color area collected during the image acquisition represents approximately 25% of the fully filled color area present in the final image.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A color Doppler ultrasound imaging method, the method comprising:
   acquiring a plurality of sparse color Doppler ultrasound image frames and B-mode ultrasound image frames;
   pre-processing a current sparse color Doppler ultrasound image frame and a B-mode ultrasound image frame of the plurality of sparse color Doppler and B-mode ultrasound image frames;
   estimating a vector flow based on the pre-processed current sparse color Doppler and B-mode ultrasound image frames, wherein the estimating of a vector flow comprises solving a flow vector field (u) in a whole field of view of the image frames by applying an optimization framework to the current sparse color Doppler image frame, wherein the optimization framework comprises a mask (M) adapted to define a sparse area of observed color Doppler measurements (m) within the current sparse color Doppler image frame, such that the solved flow vector field (u) is compatible with the observed color Doppler measurements (m) within the mask (M);
   generating a new color Doppler image frame based on the estimated vector flow; and
   generating an output image including the new color Doppler image frame.

2. A method as claimed in claim 1, wherein the optimization framework comprises a smoothing term.

3. A method as claimed in claim 1, wherein the optimization framework comprises a zero divergence restraint.

4. A method as claimed in claim 1, wherein the optimization framework comprises an estimated boundary velocity.

5. A method as claimed in claim 1, wherein the mask (M) is a pixel-wise weighting mask, wherein the weighting mask has a value of zero for each of those pixels in the current sparse color Doppler image frame for which no observed color Doppler measurement (m) exist.

6. A method as claimed in claim 5, wherein the weighting mask has a value ranging between zero and one for each of those pixels in the current sparse color Doppler image frame for which observed color Doppler measurement (m) exist, said value reflecting a confidence level on the observed color Doppler measurement (m) at each respective pixel.

7. A method as claimed in claim 6, wherein the confidence level is a function of the noise level at each respective pixel.

8. A method as claimed in claim 1, wherein the generating of an output image comprises overlaying the new color Doppler image frame on the current B-mode ultrasound image frame.

9. A method as claimed in claim 1, wherein the generating of a new color Doppler image frame comprises re-projecting the flow vector field (u) solved in the whole field of view of the image frames on the ultrasound beam orientation (s) along which the observed color Doppler measurements (m) have been acquired.

10. A method as claimed in claim 1, wherein the pre-processing comprises performing phase unwrapping on the current sparse color Doppler ultrasound image frame.

11. A method as claimed in claim 1, wherein the pre-processing comprises performing flow boundary segmentation on the current B-mode ultrasound image frame.

12. A method as claimed in any of claim 11, wherein the pre-processing comprises deriving a motion of a boundary between a previous B-mode image frame and the current B-mode frame based on the flow boundary segmentation.

13. A method as claimed in claim 12, wherein the derivation of the motion of the boundary is based on speckle tracking.

14. A method as claimed in claim 1, wherein the plurality of sparse color Doppler ultrasound image frames comprise 3D color Doppler ultrasound image volumes.

15. A method as claimed in claim 14, wherein the 3D color Doppler ultrasound image volumes are generated by:
   acquiring a set of sparse color Doppler ultrasound image frames at a plurality of spatial locations;
   interpolating image data between the acquired frames of the sets of sparse color Doppler ultrasound image frames; and
   generating 3D color Doppler image volumes based on the acquired image frames and the interpolated image data.

16. An ultrasound system adapted to perform color Doppler ultrasound imaging, the system comprising:
   an ultrasound probe adapted to acquire ultrasound image data;
   a processor adapted to:
      acquire a plurality of sparse color Doppler ultrasound image frames and B-mode ultrasound image frames;
      pre-process a current sparse color Doppler ultrasound image frame and a B-mode ultrasound image frame of the plurality of sparse color Doppler and B-mode ultrasound image frames;
      estimate a vector flow based on the pre-processed current sparse color Doppler and B-mode ultrasound image frames, wherein estimating a vector flow comprises solving a flow vector field (u) in a whole field of view of the image frames by applying an optimization framework to the current sparse color Doppler image frame, wherein the optimization framework comprises a mask (M) adapted to define a sparse area of observed color Doppler measurements (m) within the current sparse color Doppler image frame, such that the solved flow vector field (u) is compatible with the observed color Doppler measurements (m) within the mask (M);
      generate a new color Doppler image frame based on the estimated vector flow; and
   generate an output image including the new color Doppler image frame.

\* \* \* \* \*